United States Patent [19]

Samson

[11] Patent Number: 5,725,546
[45] Date of Patent: Mar. 10, 1998

[54] DETACHABLE MICROCOIL DELIVERY CATHETER

[75] Inventor: Gene Samson, Milpitas, Calif.

[73] Assignee: Target Therapeutics, Inc., Fremont, Calif.

[21] Appl. No.: 265,580

[22] Filed: Jun. 24, 1994

[51] Int. Cl.$^6$ .................................................. A61M 29/20
[52] U.S. Cl. ...................................... 606/191; 606/194
[58] Field of Search ................................ 606/151, 213, 606/108, 191

[56] References Cited

U.S. PATENT DOCUMENTS

| | | |
|---|---|---|
| 4,643,184 | 2/1987 | Mobin-Uddin . |
| 4,739,768 | 4/1988 | Engelson . |
| 4,813,934 | 3/1989 | Engelson et al. . |
| 4,884,579 | 12/1989 | Engelson . |
| 4,968,296 | 11/1990 | Ritch et al. . |
| 4,994,069 | 2/1991 | Ritchart et al. . |
| 5,098,374 | 3/1992 | Othel-Jacobson et al. . |
| 5,108,407 | 4/1992 | Geremia et al. . |
| 5,108,420 | 4/1992 | Marks . |
| 5,122,136 | 6/1992 | Guglielmi et al. . |
| 5,180,362 | 1/1993 | Worst . |
| 5,217,484 | 6/1993 | Marks . |
| 5,234,437 | 8/1993 | Sepetka . |
| 5,250,071 | 10/1993 | Palermo . |
| 5,256,146 | 10/1993 | Ensminger et al. . |
| 5,261,916 | 11/1993 | Engelson . |
| 5,263,964 | 11/1993 | Purdy . |
| 5,290,295 | 3/1994 | Querals et al. . |
| 5,304,195 | 4/1994 | Twyford, Jr. et al. . |

*Primary Examiner*—Michael Buiz
*Assistant Examiner*—Daphna Shai
*Attorney, Agent, or Firm*—Morrison & Foerster LPP

[57] ABSTRACT

This invention is a surgical instrument, and specifically is a device for delivering embolic coils to a selected site within the vasculature of a human body. This instrument uses, and may include, the catheter used to place the embolic coil. In particular, the device is made up of a pusher wire having a distal tip which is configured to engage the proximal end of an embolic coil. The device may also include a cylindrical pusher which coaxially surrounds at least a portion of the pusher wire and cooperates in the disengagement of the coil from the pusher wire and the ejection of the vasoocclusive coil into the selected vascular site. The pusher wire's engagement tip may be of any selected and convenient shape, and may be grooved, if so desired, to enhance the engagement joint strength.

6 Claims, 1 Drawing Sheet

DETACHABLE MICROCOIL DELIVERY CATHETER

FIELD OF THE INVENTION

This invention is a surgical instrument, and specifically is a device for delivering embolic coils to a selected site within the vasculature of a human body. This instrument uses, and may include, the catheter used to place the embolic coil. In particular, the device is made up of a pusher wire having a distal tip which is configured to engage the proximal end of an embolic coil. The device may also include a cylindrical pusher which coaxially surrounds at least a portion of the pusher wire and cooperates in the disengagement of the coil from the pusher wire and the ejection of the vasoocclusive coil into the selected vascular site. The pusher wire's engagement tip may be of any selected and convenient shape, and may be grooved, if so desired, to enhance the engagement joint strength.

BACKGROUND OF THE INVENTION

The endovascular treatment of a variety of vascular maladies throughout the body is an increasingly more important form of therapy. Catheters have been used to place various treatment materials, devices, and drugs within the arteries and veins of the human body. Examples of these devices and their use in such treatments are shown in U.S. Pat. No. 4,994,069, to Ritchart et al. Examples of vasoocclusive devices which are mechanically detachable from installation devices provided within vascular catheters include those found in U.S. Pat. No. 5,250,071, to Palermo, issued Oct. 5, 1993; in U.S. Pat. No. 5,261,916, to Engelson, issued Nov. 16, 1993; and U.S. Pat. No. 5,304,195, to Twyford et al, issued Apr. 19, 1994. These show methods and devices for delivery of coils or wires within the human body to sites such as aneurysms, so to occlude those sites. The coils delivered in such a manner may be of regular or helical configuration or may assume a random convoluted configuration at the site. The coils normally are made of a radiopaque, biocompatible materials such as platinum, gold, tungsten, alloys of these materials, stainless steels, various plastics, and the like.

In treating aneurysms, it is common to place a significant length of coil within the aneurysm. The coils occlude the site by posing a physical barrier to blood flow and by promoting thrombus formation at the site.

Coils have typically been placed at the desired site within the vasculature using a catheter and a pusher. The site is first accessed by the catheter—often with the help of a guidewire. In treating peripheral or neural conditions requiring occlusion, the sites are accessed with flexible, small diameter catheters such as those shown in U.S. Pat. Nos. 4,739, 768 and 4,813,934. As noted above, the catheter may be guided to the site through the use of guidewires such as those shown in U.S. Pat. No. 4,884,579 or by flow-directed means such as balloons placed integrally at the distal end of the catheter. Use of guidewires involves the placement of relatively long, torqueable proximal wire sections within the catheter attached to more flexible distal end wire sections designed to be advanced across sharp bends and vessel junctions. The guidewire may be visible using fluoroscopy, particularly if it is encased in a radiopague material. The radiopacity allows the attending physician to guide the catheter through extremely tortuous vessels, even when surrounded by soft tissues such as found in the liver or brain.

Once the site has been reached, the catheter lumen is cleared by removing the guidewire (if a guidewire has been used) and the coils placed into the proximal open end of the catheter and advanced through the catheter with a pusher. Pushers may be guidewire-like devices having distal ends that are adapted to engage and push the coils through the catheter lumen as the pushers advance through the catheter. When the coil reaches the distal end of the catheter, it is discharged from the catheter by the pusher at the vascular site. This technique of discharging the coil from the distal end of the catheter has a number of undesirable limitations. First, because of the plunging action of the pusher and coil, the possibility of miss-positioning the coil near the chosen site exists. Second, once the coil has left the catheter, it may be difficult to reposition or to retrieve the coil if such is necessary.

A number of techniques have been developed to enable accurate placement of coils within a vessel. In one excellent technique found in U.S. Pat. No. 5,122,136 to Guglielmi et al., the coil is bonded via a metal-to-metal joint to the distal end of a pusher. The pusher and coil are made of dissimilar metals. The coil-carrying pusher is advanced through the catheter to the selected site, and a low-voltage electrical current is passed through the pusher coil assembly. The current causes the joint between the pusher and the coil to be severed via electrolysis. The pusher may then be retracted leaving the detached coil at a specific exact position within the vessel.

Another technique involving mechanical detachment of embolic coils is found in U.S. Pat. No. 5,261,916, to Engelson. In that patent, a coil having an enlarged portion is mated with a pusher having a key way adapted to receive that enlarged portion on the distal portion of the pusher. A sleeve is used to hold the coil end member within the pusher key way. The coaxial member is moved by sliding once the coil has reached the desired site and the pusher with its key way is disengaged from the coil.

Another mechanical device is shown in U.S. Pat. No. 5,234,437, to Sepetka. This patent shows the deployment of a vasoocclusive coil by the use of an independently placed, threaded section mounted on the outside of the pusher. The device meshes with the wires of the helical coil and may be withdrawn either by simply pushing with a sleeve found without the pusher wire or, presumably, by unscrewing the pusher from the distal end of the coil. This disclosure does not suggest the use of an engageable distal tip on the guidewire which is formed by grooves within the tip itself.

Another method of placing an embolic coil is shown in U.S. Pat. No. 5,108,407. The patent shows the use of a device in which embolic coils are separated from the distal end of a catheter by the use of heat-releasable adhesive bonds. Laser energy is transferred to a fiber optic cable to heat the adhesive bond and sever the coil from the pusher wire.

There are a number of ways to place an implantable device within the human body.

For instance, the concept of using a piece of hollow tubing to place a body implant is well known. For instance, U.S. Pat. No. 4,643,184, to Mobin-Uddin, shows an embolus trap for placement in the human body. The device for deploying the embolus trap includes a guidewire and a cylindrical capture cage which prevents the embolus trap from expanding until it reaches an appropriate place within the vasculature.

Similarly, Ritch et al., U.S. Pat. No. 4,968,296, shows a device for draining fluid from the eye so to treat glaucoma. Again, the drainage implant is mounted on a wire. A hollow plunger is used to hold the implant in position as the wire is withdrawn.

3

The Worst invention, U.S. Pat. No. 5,180,362, shows a drainage device similar in concept to that shown in Ritch et al. above. A hollow needle containing a coil-like drain is inserted into the eye, and the helix is ejected using an ejector. The ejector is just said to be a rod. Engagement of the coil is not mentioned in the patent.

The disclosure in Purdy, U.S. Pat. No. 5,263,964, shows a coiled attachment apparatus in which a coil is attached to a guidewire or coil wire by glue, solder, or some other means. A tubular sheath is passed over the guidewire, and the coil is released by pulling on the guidewire while the sheath bears against the coil.

None of these disclosed devices suggests the use of a pusher wire which is simply press-fit into the proximal end of the vasoocclusive coil. Nor do any of these disclosures show a pusher having serrations or grooves in the tip of the pusher wire itself.

SUMMARY OF THE INVENTION

This invention is a device for placing coils within the vasculature of a mammalian body so as to occlude the selected site. The device includes a pusher having a distal engaging tip and a coil having an open proximal end which may be engaged by that tip. The pusher preferably is a guidewire having a ground conical distal tip which may further have circumferential or helical grooves in that conical region. The grooves and the conical tip are used to engage the interior of the vasoocclusive coil and hold it during axial traversal of the catheter. The engaging tip holds the vasoocclusive coil with such strength that it may be moved axially in either direction in a catheter without fear of loss. The engaging tip may be cylindrical in form and, again, may have either helical grooves or circumferential grooves in the cylindrical area (which is to fit inside the proximal end of the vasoocclusive coil) so to hold the vasoocclusive device as it is moved axially through the catheter or vasculature.

DESCRIPTION OF THE INVENTION

Figure 1:
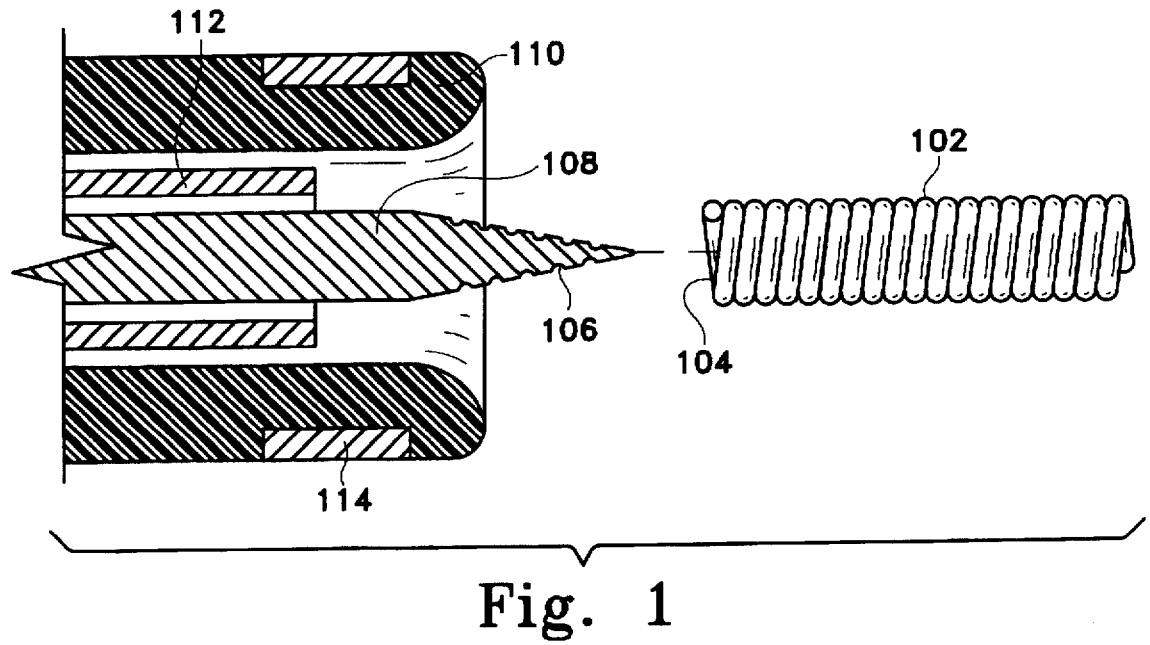
FIG. 1 shows, in high magnification, a side view, cross section of a generic device made according to the invention.

FIG. 1 shows an overall assembly (100) of components which make up a broad variation of the invention. In particular, a helical coil (102) is shown as the vasoocclusive device. The proximal end (104) of the vasoocclusive coil (102) is open and adapted to receive and engage the engageable tip (106) found on pusher core wire (108). Engageable tip (106) is shown in this drawing to be conical and to have an axis which runs generally in coincidence with the axis of the pusher wire (108). As will be described below in more detail, the engageable tip (106) may be grooved or may be left to be smoothed or may be left in a semi-machined or sanded condition to achieve good adherence to the interior of coil (102) upon insertion. The engageable tip (106) is to enter the open end of coil (102). The coil will typically have an open lumen for a significant distance from its proximal end (104).

The coil itself should be of a size sufficiently small that it may be advanced through a catheter (110) and desirably is

4 about the same diameter as cylindrical pusher (112). The coil should also be appropriately sized for accessing the targeted vascular site. For instance, when accessing a brain aneurysm in a small vessel, an appropriately sized catheter is usually quite small and very flexible. The coil in such a situation must be sufficiently small to fit through the catheter and pass out the distal end of the catheter at the treatment site.

The coil is desirably made up of radiopaque, physiologically compatible material. The material may be platinum, gold, tungsten, alloys of these metals, or stainless steel or various polymers. These polymers may be used either as coil material per se or in conjunction with metallic markers so to provide sufficient radiopacity.

The size of the coil in its constituent windings will depend upon the use to which the coil will be put. For occluding peripheral or neural sites, the coils will typically be on the smaller side, e.g., of 0.05 to 0.15" diameter wire (platinum or platinum/tungsten alloy) that is wound to have an inner diameter of 0.15 to 1.5" with a minimum pitch. By "minimum pitch" we mean to say that the pitch is equal to the diameter of the wire used in the coil. The length of such coils would normally be in the range of 0.5 to 100 cm, preferably 0.5 to 40 cm. If desired, the coil may be formed in such a way that the coil is essentially linear as it passes through the catheter and yet assumes a randomly oriented condition once it is released from the distal end of the catheter. A discussion of this variation may be found in U.S. Pat. No. 4,994,069, to Ritchart et al., the entirety of which is incorporated by notice.

It is also within the purview of this invention that filamentary braids, tassels, or looping ties be placed on the exterior surface of the coils. These filamentary materials improve the ability of the coil to form a thrombus at the elected site.

Further shown in FIG. 1 is a catheter body (110) and coaxial tubular pusher (112). Finally a radiopaque band (114) is also depicted in the figure.

The device shown in FIG. 1 is shown as it would be seen by a person either loading the coil (102) onto engageable tip (106) of pusher wire (108) or, conversely, just after the coil has been cut loose. As is described in many of the patents discussed above, a good way to utilize this device is to load the coil (102) onto distal end (106) of pusher wire (108) and retract the coil (102) within the lumen of catheter (110). Obviously pusher (112) is also retracted within the catheter body (110).

The device may be employed by using known techniques for placement of catheters. For instance, catheter (110) may be put in place by use of a guidewire, the guidewire then being withdrawn, and the coil (102) introduced into the catheter (110) lumen followed by a pusher wire (106) and pusher tubing (112). Once the coil is carefully placed at the desired site, a variety of ways of using the device may then be utilized. For instance, pusher core wire (108) may be "unscrewed" from the interior of coil (102). The pusher tubing (112) may be used in this instance to prevent the rotation of the coil (102) as pusher (108) is screwed and withdrawn from the catheter body.

Figure 2:
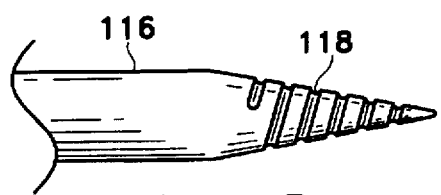
FIGS. 2 and 3 show magnified side views of two conical pusher wire tips made according to this invention.

FIG. 2 shows a variation of the distal tip of pusher wire (116) in which the engaging end includes helically placed grooves (118) on that engaging section. Desirably the spacing of these grooves (118) is such that it matches the pitch of the vasoocclusive coil (102 in FIG. 1) and thereby increases the holding capacity of the resulting joint.

It may be apparent that the overall diameter of the vasoocclusive coil (102) as it engages the distal tip of the pusher wires is slightly increased. The amount of increase must be balanced in such a fashion that it does not bind with the interior diameter of the catheter in order to fulfill the major goal of the inventive device. That is to say, when the pusher core wire is locked to the vasoocclusive coil (102) without excessively expanding the diameter of a vasoocclusive coil (102), the device operates quite well in that it does not cause kinking of the catheter as it is traversed through the catheter's lumen. Consequently, some thought must be had in choosing the size and slope of the conical engaging end.

Figure 3:
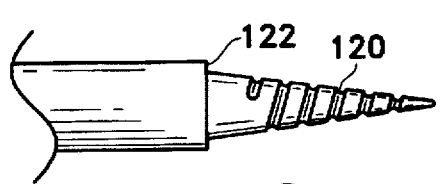

FIG. 3 shows a conical engaging end (120) also having helical grooves in the cone face. This variation, however, has shoulder (122) at the base of the cone. This shoulder should allow the vasoocclusive coil (102) to mesh with cone (120) without excessive splaying of the coil. It is a way to control the increase of a radius which occurs when the engageable end (116) is engaged in the proximal end of the vasoocclusive coil.

It should be apparent that the variations of the conical engaging end shown in FIGS. 1, 2, and 3 may utilize grooves placed in the conical face which are merely concentric and not helical in form. The engageability of this variation is not quite as good as with the helical grooves portrayed in the figures, but certainly they are acceptable and somewhat easier to place on the distal end of the pusher wire.

Figure 4:
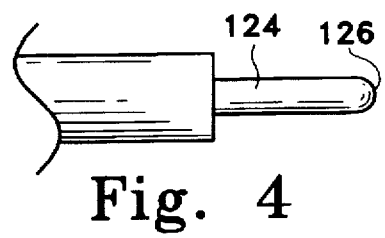
FIGS. 4, 5, and 6 show highly magnified inside views of cylindrical engaging tips made according to the invention.

FIG. 4 shows still another variation of the pusher wire in side view. Located on the distal tip is a generally cylindrical engagement end (124) having a rounded tip (126). As an aside, the conical tips described above may also have a rounded tip such as (126) found in this drawing. In any event, the diameter of cylindrical engaging tip (124) is slightly larger than the lumen of the coil used as the vasoocclusive device (e.g., 102 and FIG. 1). The concept here is that when the coil is pushed over the receiver end, there should be a slight compression fit.

Figure 5:
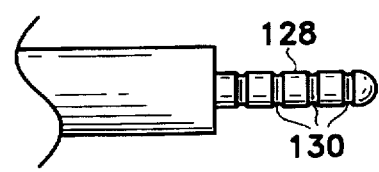

FIG. 5 shows a cylindrical engaging end (128) similar to that seen in FIG. 4 but in which the engaging end has circumferential grooves (130) so to cooperate with the terms of the helical coil and provide a bit higher measure of locking with the engaging end (128).

Figure 6:
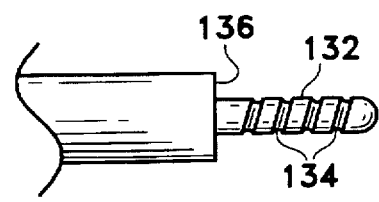

Similarly, FIG. 6 shows another variation of the cylindrical engaging tip (132) having a helical thread (134) cut or otherwise placed into the tip so to engage the vasoocclusive helically wound coil with even greater tenacity. Again, the outer diameter of the vasoocclusive coil as it nestles up against shoulder (136) should not exceed the diameter of the pusher wire at that point. In this way, a smooth transition is had and it is less likely to cause kinking or other problems within the delivery catheter.

Although the discussion of this invention has, in general, emphasized the structure at the distal portion of the pusher wire and the proximal end of the vasoocclusive device, it should be emphasized that the invention is not so limited. The catheter and pusher must be of such a length that they are capable of being advanced through the vasculature to the target site without a problem. The pusher wire and tubular pusher shown above in FIG. 1 must be of a length sufficient to push the coil to be delivered completely through the catheter and, indeed, typically out of the other end into the region of the site where the occlusion is to be created so that the pusher can then be disengaged and the pusher and catheter assembly removed without significant movement of the vasoocclusive coil.

Modifications of the device described above and methods of using it in keeping with this invention that are apparent to those having ordinary skill in this mechanical and surgical instrument design art and related fields are intended to be within the scope of the claims which follow.

I claim as my invention:

1. A combination pusher-coil for occluding a vessel at a selected vascular site within the vessel comprising:
   (a) a helically wound coil having a proximal end and an opening in that coil proximal end for accepting an engaging tip on a pusher wire, and
   (b) a pusher wire having a longitudinal axis and a distal engaging tip,
   said distal engaging tip having an outer surface with grooves formed therein said outer surface is unitary with the distal engaging tip, said distal engaging tip for entering the opening in the proximal end of the helically wound coil.

2. The combination of claim 1 where the coil and the pusher wire are engaged.

3. The combination of claim 2 further comprising a catheter body coaxial to at least a portion of the pusher wire.

4. The combination of claim 1 additionally comprising a pusher tube coaxial to the pusher wire and proximal to the distal pusher wire engaging tip for pushing upon the proximal end of the helically wound coil.

5. The combination of claim 9 further comprising a catheter body coaxial to at least a portion of the pusher wire.

6. The combination of claim 1 further comprising a catheter body coaxial to at least a portion of the pusher wire.

* * * * *

UNITED STATES PATENT AND TRADEMARK OFFICE

CERTIFICATE OF CORRECTION

PATENT NO. : 5,725,546

DATED : March 10, 1998

INVENTOR(S) : Gene Samson

It is certified that error appears in the above-identified patent and that said Letters Patent is hereby corrected as shown below:

In column 6, claim 1, line 32, insert -- helical -- before the word "grooves".

Signed and Sealed this

Third Day of November, 1998

Attest:

BRUCE LEHMAN

Attesting Officer        Commissioner of Patents and Trademarks